(12) United States Patent
Bach et al.

(10) Patent No.: US 6,444,831 B2
(45) Date of Patent: Sep. 3, 2002

(54) PROCESS FOR THE CODIMERIZATION OF POLYUNSATURATED FATTY SUBSTANCES AND OLEFINS BY IRON COMPLEXES

(75) Inventors: Ingrid Bach, Rueil Malmaison; Gérard Hillion, Herblay; Héléne Olivier, Rueil Malmaison, all of (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 52 days.

(21) Appl. No.: 09/745,436

(22) Filed: Dec. 26, 2000

(30) Foreign Application Priority Data

Dec. 24, 1999 (FR) .............................. 99 16508

(51) Int. Cl.$^7$ ................................. C09F 7/06
(52) U.S. Cl. .......................... 554/27; 554/26
(58) Field of Search ..................... 554/26, 27

(56) References Cited

U.S. PATENT DOCUMENTS 6,153,772 A * 11/2000 Hillion et al. ............... 554/26

FOREIGN PATENT DOCUMENTS

| FR | 2 766 482 |   | 1/1999 |
| FR | 2766482 | * | 1/1999 |

* cited by examiner

Primary Examiner—Deborah D. Carr
(74) Attorney, Agent, or Firm—Millen, White, Zelano & Branigan, P.C.

(57) ABSTRACT

To obtain branched compounds from fatty substances, simple olefins are reacted on polyunsaturated esters, which may or may not be conjugated, in the presence of an iron catalytic system, whereby the products that are obtained, primarily mono-addition compounds, can be hydrogenated and transformed into various compounds that can be used in particular as a base for surfactants, emulsifiers, emollients, lubricants or heavy metal salts.

17 Claims, 3 Drawing Sheets

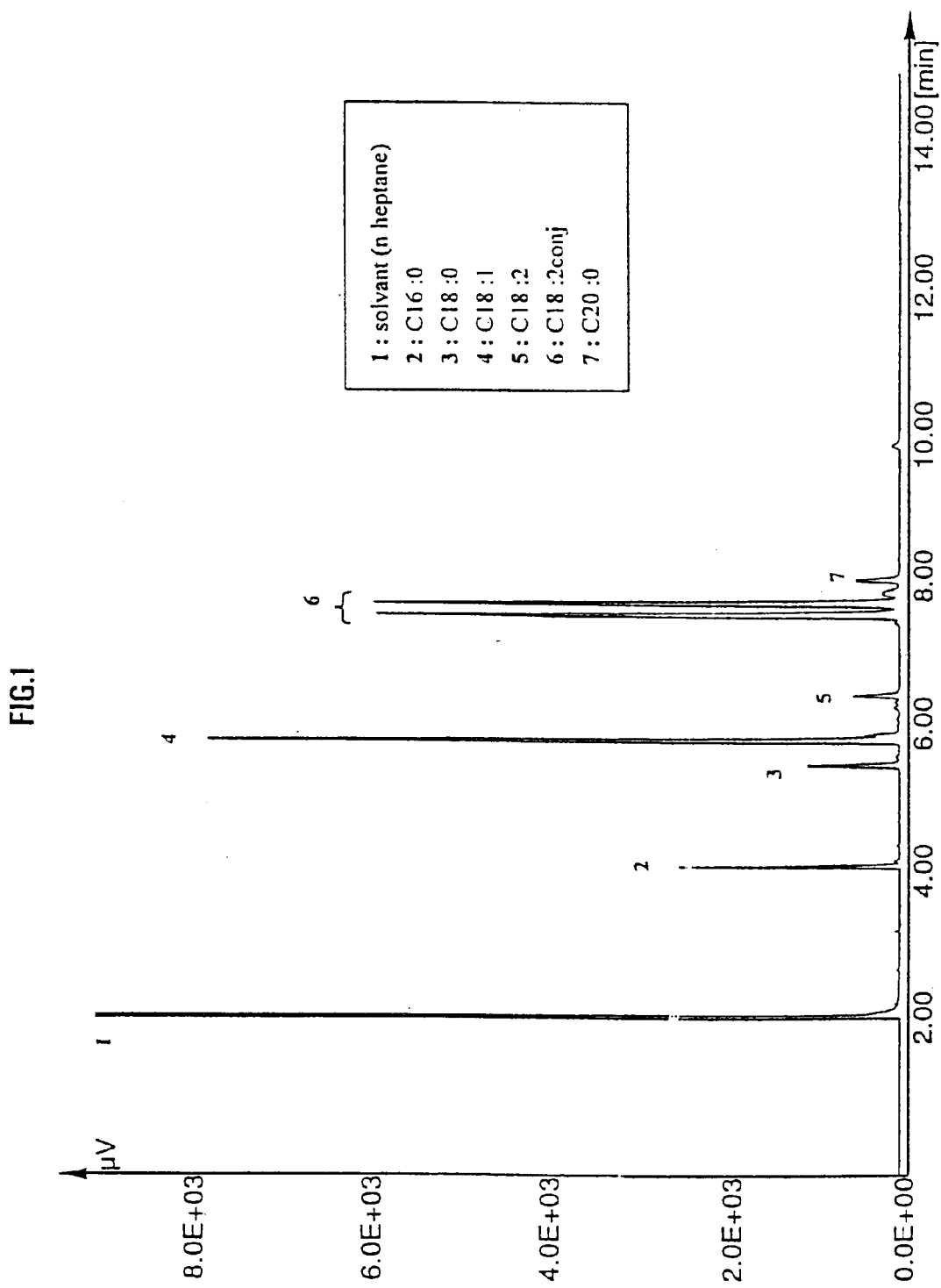

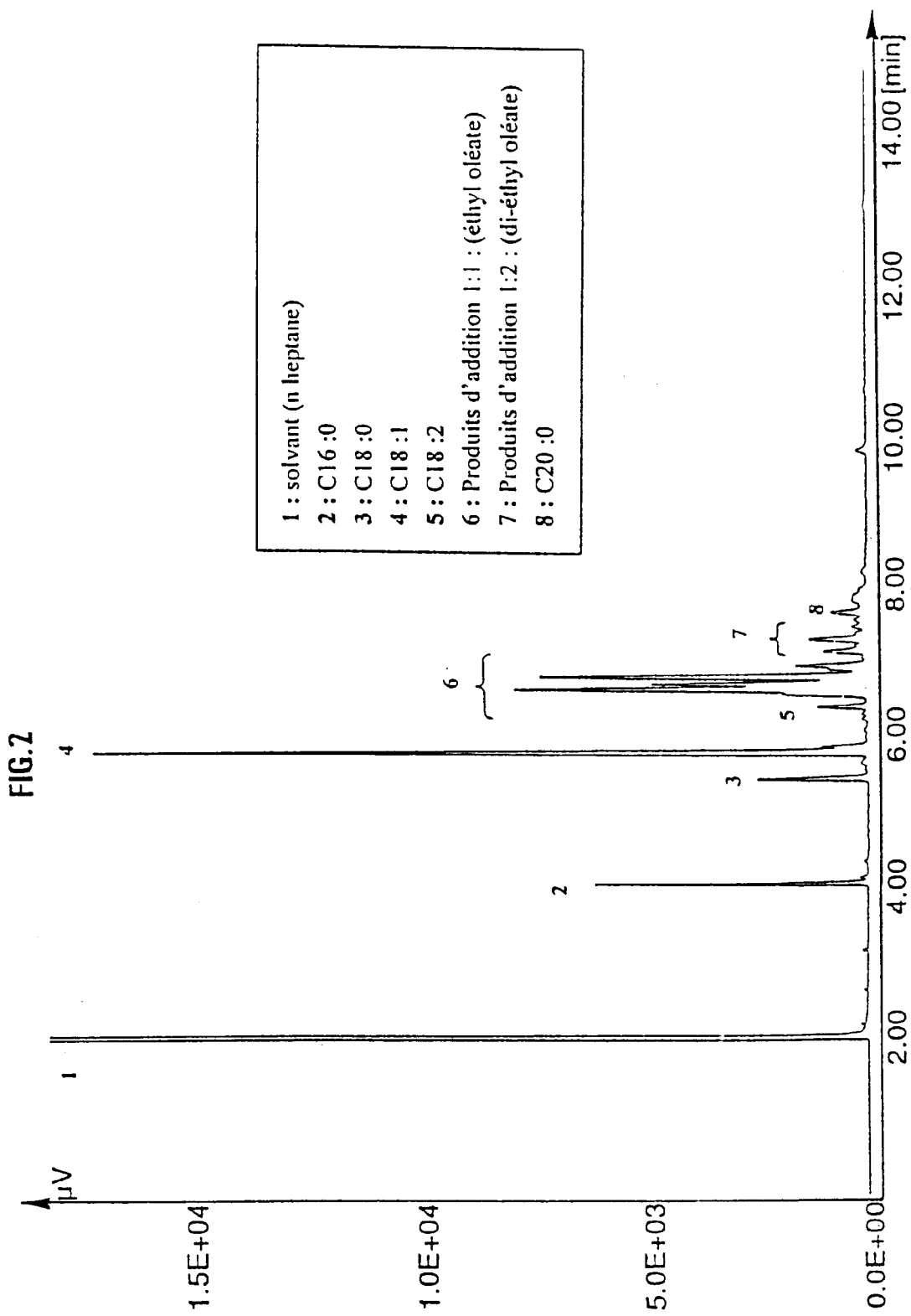

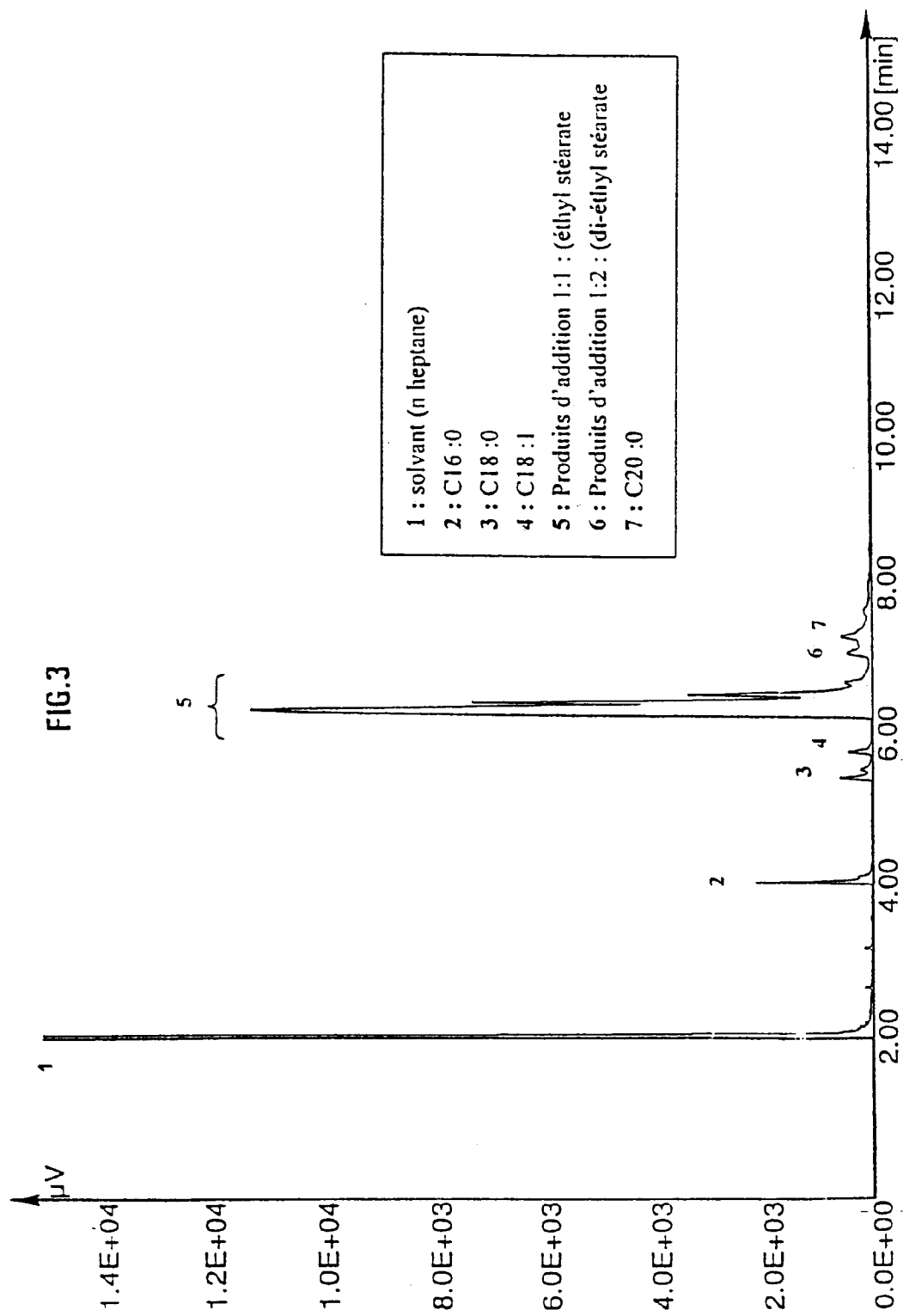

PROCESS FOR THE CODIMERIZATION OF POLYUNSATURATED FATTY SUBSTANCES AND OLEFINS BY IRON COMPLEXES

The invention has as its object a new process for obtaining chemical compounds that are obtained from polyunsaturated fatty substances, said compounds characterized by the presence, along the linear hydrocarbon-containing chain, of a branch of at least two carbon atoms.

These compounds are obtained by adding olefins to the polyunsaturated fatty substances that may or may not be conjugated, in the presence of an iron catalytic system.

The unsaturated codimers that are obtained can be hydrogenated, and saturated fatty substances that are characterized by a melting point that is generally below –30° C., significant thermostability, and desired surfactant properties are then obtained.

The presence of branches in the fatty substance-based compounds, mainly when these branches are located toward the center of the linear chains that comprise 14 to 18 carbon atoms, is reflected by a certain number of remarkable properties, such as, for example:

The very significant lowering of the melting points, pour points, cloud points and a considerable increase of the viscosity of the branched fatty substances relative to the same linear compounds (unbranched). This property is used in, for example, the lubricants, fats, or plasticizers where esters of fatty substances, salts or esters of branched alcohols, whose acid may be organic or mineral, are used.

The reduction of the surface and interfacial tension, characteristics still sought in the field of surfactants and emulsifiers. This reduction makes it possible to obtain very low CMC (critical micellar concentration).

The inhibition of the crystallization of branched soaps that may or may not be mixed with standard soaps, which makes it possible to obtain transparent soaps.

An increase of the hydrophilicity, which makes the branched compounds more soluble or more wettable. A possible use would be to use quaternary salts of branched fatty acids in the emollients where the softening is on a par with a certain wettability.

A modification of the surface of the molecule, a surface that is characterized by gaps that are produced by the presence of branches. The cosmetic application of this property makes it possible to consider skin cream formulas that allow water vapor to pass, for example bases that consist of branched acid esters or even esters in which the acid and the alcohol are both branched.

The increased solubility of heavy metal salts with branched acids, which makes them soluble either in water or in certain organic solvents. The applications are multiple, such as drying agents in paints, like pigments, in the extraction of metals, anticorrosion where it is possible to use salts of calcium, alkanolamines, or even amines as active agents. Likewise, the branched acid salts offer a greater compatibility of certain mineral batches with polymers, which makes it possible to increase the ratio of feedstocks in the plastics.

The bactericidal or bacteriostatic effect that is more or less pronounced according to the nature of the bacteria and the number or the magnitude of the branches makes it possible to protect the creams from bacterial attack or to replace the quaternary salts in the formulations that may or may not be basic. Another use exists as an inhibitor of water evaporation where, for example, compounds such as a branched alcohol or a branched acid monoglyceride make it possible to delay the biodegradability and therefore to conserve the inhibitor.

The reaction of olefins with butadiene or other dienes has been known for a long time and was examined several times. The codimerization of butadiene with ethylene leads to 1,4-hexadiene; codimerization of ethylene with isoprene to methyl-3 hexadiene; and, finally, by codimerization of ethylene with piperylene, vinyl-2-pentene is obtained. Many catalysts are used to carry out these reactions. It is possible to cite, for example, rhodium, ruthenium, palladium, cobalt, iron, or nickel systems. Systems with a titanium base have been described (Connel, Laurence G.-Ann. N.Y. Acad. Sci. (73), 214, 143–9) to catalyze the formation of vinylcyclobutane from ethylene and butadiene.

U.S. Pat. No. 3,927,137 and German Patent Application DE-A-39 06 434 describe the use of catalytic systems with a base of iron salts combined with imine- or diimine-type ligands for codimerizing α-olefins of low molecular weight with conjugated diolefins.

In contrast, the addition of an olefin to functional dienes has rarely been described. Patent U.S. Pat. No. 3,742,080 points out the possibility of adding ethylene to dienes, of which one or two hydrocarbon-containing chain ends are substituted by halogen atoms or alkoxy groups.

It is also known that an olefin can react on a conjugated diene or triene compound according to a Diels-Alder-type reaction. For example, R. E. Beal et Coll. [JAOCS 52, 400 (1975)] described the addition of ethylene to the polyunsaturated fatty substances by simple heating to a temperature of 290° C. Thus, a compound that has an unsaturated cycle with 6 carbon atoms in its hydrocarbon-containing chain is obtained from methyl and ethylene linoleate. After hydrogenation, these compounds have advantageous properties. Their melting point, however, which is above 10° C., is still too high to allow them to be used as lubricants.

Another method for obtaining branched compounds of fatty substances is known. It consists in reacting, according to a Wittig-type reaction, a ketone, such as, for example, the methyl ester of 12-oxo octadecanoic acid with an ylide, for example, the link $P(\Phi)_3$=$CHCH_3$, where $\Phi$ represents a phenyl radical. The compound $CH_3(CH_2)_5C$(=$CHCH_3$)$(CH_2)_{10}COOCH_3$, which can be hydrogenated into methyl ethyl-12-octadecanoate, is then obtained [see D. G. Chasin et Coll., Chem. Phys. Lipids (71) 6, 8–30].

In nature, the presence of branched saturated compounds of fatty substances that are found in Koch bacilli, for example, or, with another length of hydrocarbon-containing chain, in mutton fat has been pointed out.

Finally, it is known that the products that are referred to as "isostearic" contain traces of compounds that carry ethyl- or vinyl-type branches.

Recently, international patent applications WO-A-91/11428, 91-11427, 91/11426, and 91/11425 describe obtaining branched fatty substance compounds by a catalytic process. The addition of olefin, such as ethylene, propylene or butene-1, to the polyunsaturated fatty substance, a linoleic acid ester, for example, is catalyzed by a system with a base of rhodium, iridium, palladium, or ruthenium. The systems with rhodium, which are the only ones to have been described in an obvious way, are not very active, however.

U.S. Pat. Nos. 5,476,956 and 5,434,282 describe the use of a very specific rhodium catalytic system that makes it possible to accelerate the addition of olefin to the fatty substance dienes, particularly conjugated dienes, by a factor of 50 to 100. This process, however, is still very difficult to apply on a large scale due to excessive rhodium consumption.

FR-B-2 766 482, in the name of the applicant, describes a cobalt catalytic system that consists in reacting simple olefins, for example ethylene and propylene, in polyunsaturated esters, for example methyl linoleate, which may or may not be conjugated, to obtain branched esters. The branched compounds that are obtained can be hydrogenated and used, among other things, as lubricant bases. In this application, a process for obtaining a codimer is described. Co-catalysts can optionally be introduced, such as, for example, transition metals of iron, nickel, copper, rhodium or palladium type. These co-catalysts make it possible to catalyze the conjugation, if a start is made from an unconjugated polyenic ester and therefore to accelerate the reaction speed.

The main improvement that this invention provides consists in a very significant increase in reactivity that is obtained by use of a catalytic system with an iron base relative to the preceding system that used primarily a cobalt system. By working in the same conditions, 10 to 15× more mono-addition products are obtained.

From an economical standpoint, the catalytic system that is described in this invention could turn out to be of great interest with a view to optional industrial development.

The so-called "polyunsaturated fatty substance" compound that is employed in the reaction on which the process of the invention is based is generally a compound that comprises, on the one hand, at least two ethylene bonds, whereby these bonds can be conjugated or can be conjugated two by two, and, on the other hand, a carboxylic group such as the one that is present in fatty acids that have 18 to 26 carbon atoms. Litmus, safflower, fish, linseed, soybean, oiticica, cottonseed, colza, Chinese wood, nut, corn, linola, and grape seed oils and generally all the oils or their derived esters that comprise polyunsaturated compounds are conceivable as raw materials.

The diene, triene, or polyene fatty acids that are considered can be used as such or preferably in the form of their esters that are formed either from fatty acids or oils by reaction with monofunctional alcohols, such as methanol or ethanol, difunctional alcohols, such as neopentylglycol, trifunctional alcohols, such as trimethylolpropane, and polyfunctional alcohols, such as sorbitol, polyglycerols, pentaerythritol and sugars. The oils themselves are possible substrates.

These esters can be used as they are or partially and/or totally conjugated. In other words, they can contain at least two double ethylene bonds that may or may not be separated by a methylene group. Among the best-known processes for conjugating double bonds, it is possible to cite those that use alkaline alcoholates in the presence or absence of a solvent. It is possible in this case to obtain up to 99% of fatty substance that is conjugated relative to the polyunsaturated fatty substance that is initially present in the oil.

Other conjugating catalytic systems that employ ruthenium or carbonyl iron complexes are known. The iron system can itself be conjugating in some cases. It is possible, however, to attach a co-metal to it to accelerate the conjugation reaction.

The monoolefinic compound that is employed in the reaction may consist of any reactive olefin that is selected from among the ordinary monoolefins (monoolefinic hydrocarbons), such as, for example, ethylene, propylene, or butene-1.

The object of this invention is therefore a new process for obtaining a branched fatty substance, in the form of a codimer, that is characterized in that at least one monoolefinic compound is added to a fatty substance that comprises at least two ethylene bonds that may or may not be conjugated, in the presence of a catalytic system that comprises at least one iron compound, at least one reducing compound, and at least one ligand that contains phosphorus, arsenic, antimony or nitrogen.

The iron compound can be a bivalent or trivalent inorganic or organic iron compound that corresponds to the formula Fe $X_n$, in which n=2 or 3, and X represents a halide, a thiocyanide, a sulfate, a nitrate, an alcoholate, a carbonate, a carboxylate, a diketone, a betacetocarboxylic acid ester, a hydroxyl, an alkyl or alkenyl group (in the organo-iron compounds) or else a hydride. Particular examples of usable iron compounds are iron(II) bisacetylacetonate, iron(III) trisacetylacetonate and iron(II) and (III) octoate.

The usable iron reducing compounds are most often selected from among:

the organoaluminum compounds of general formula $AlR_X(X)_{3-X1}$ where R is hydrogen or an alkyl group, for example methyl, ethyl, isopropyl, butyl, isobutyl or terbutyl, or an alkoxy group; X is a halogen atom; and x is equal to 1 or 2, the organo-magnesia, aluminoxanes, sodium borhydride and varied alkaline hydrides, such as $LiAlH_4$ and $NaAlH_4$ themselves or their derivatives that are obtained by substituting 1 to 3 hydrogen atoms per 1, 2 or 3 alkoxy groups, for example $LiAlH_3(OR)$, $LiAlH_2(OR)_2$ and $LiAlH(OR)_3$, where R is an alkyl group, for example, methyl, ethyl, isopropyl, butyl, isobutyl or terbutyl.

The ligand can be selected:

from among the derivatives of phosphorus, arsenic or antimony that correspond in general to the formulas:

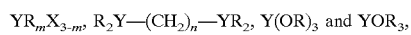

in which Y=P, As or Sb; m=0, 1, 2, or 3; R=alkyl, aryl or substituted aryl; X=halogen, and n=0, 1, 2, 3 or 4; and from among the nitrogen-containing ligands, such as the amines and polyamines, imidazole, the substituted imidazoles, pyrrole and the substituted pyrroles, pyrazoles, amidic derivatives, imines or diimines (produced, for example, by reaction of glyoxal with a derivative of the aniline that is substituted on the aromatic core), and finally the pyridinic derivatives.

Particular examples of ligands are those that have for general formulas:

with R'=H or $CH_3$, n=1, 2, 3 or 4 and R=alkyl, aryl or aryl that is partially substituted by 1, 2, 3 or 4 methyl, ethyl, isopropyl or methoxy groups.

The following developed formulas illustrate some of these products:

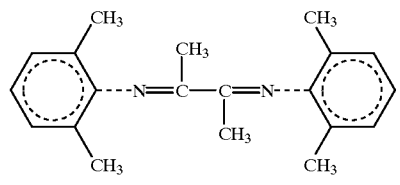
2,3-bis(2,6 dimethylphenylimino) butane (1)

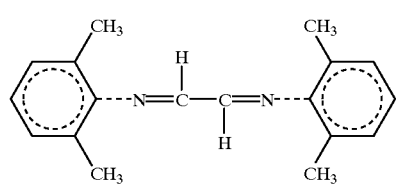
bis(2,6 dimethylphenylimino) ethane (2)

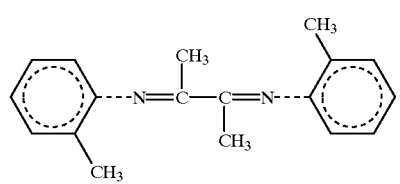
2,3-bis(methyl-2 phenylimino) butane (3)

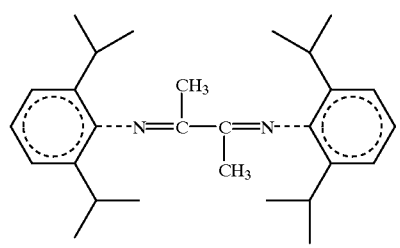
2,3-bis(2,6 diisopropylphenylimino) butane (4)

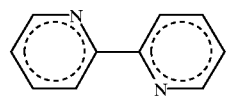
2,2 bipyridyl (5)

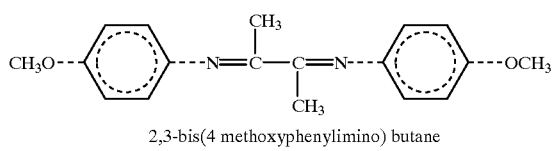
2,3-bis(4 methoxyphenylimino) butane (6)

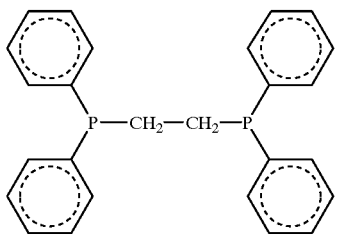
diphenylphosphinoethane (dppe) (7)

It is optionally possible to use an organic compound that acts as a solvent; as solvents, it is possible to use the aliphatic or aromatic hydrocarbons, the ethers, esters, halogenated hydrocarbides and, at low concentration, sulfoxides and amides; the reaction can also be carried out in the absence of added solvent; it is then the ester of which a portion does not react with the olefin that acts as a solvent.

It is also possible to add to the codimerization catalyst a salt of another transition metal (for example, Co, Ni, Cu, Rh, Pd, Mn, Mo, W or V, preferably Ni, Cu, Rh or Pd), which is introduced in a smaller proportion compared to the iron and which makes it possible to accelerate the reaction, in particular when the polyunsaturated substrate with a fatty substance base does not have its double bonds in conjugated form.

The molar ratio between the ligand and the iron compound is preferably from 0.5 to 10, in particular from 0.5 to 3.

If the ligand is monocoordinating, there is an advantage in using it with a ligand/metal molar ratio of 2 to 3. If the ligand is bicoordinating, it will rather be used with a molar ratio of 1 to 1.5. The molar ratio between the reducing agent and the iron compound is generally 1 to 30, preferably 7 to 15.

According to this invention, it is possible to preform the catalytic system by reacting the iron salt, the ligand, and the reducing agent, and then to introduce it into the polyunsaturated fatty substance in the presence of the olefin.

Generally, it is preferable to add the ligand to the iron compound in the presence of unsaturated fatty substance and in the presence of olefin before the reducing agent is added. It is also possible to isolate a small complex of $FeHXL_2$ iron (where L is an imine and X is a halogen) or $FeHXL'$ (where L' is a diimine and X is a halogen) and to add a reducing agent such as an alkylaluminum or the like in the presence of the polyunsaturated fatty substance.

The catalytic composition is added to the system in a catalytic amount. This amount is expressed as being $10^{-4}$ to $10^{-1}$ mol of iron per mol of conjugated polyunsaturated fatty substance. The reaction temperature is 40 to 120° C. and preferably 50 to 70° C. The olefin pressure is 0.1 to 30 MPa, and preferably 2 to 5 MPa. The reaction times depend on the concentration and the nature of the catalyst. The reaction times can be short, for example from several minutes to several hours.

It is possible to operate according to a continuous or intermittent process. The introduction of the catalyst and esters into the reactor can be done in the presence of ethylene at low temperature or at the highest temperature directly into the reactor.

The branched fatty substances that are obtained can be hydrogenated to obtain more stable products. The hydrogenation of the olefinic compounds is carried out with a catalyst that is known for hydrogenating olefins, either, for example, Raney nickel, palladium on carbon or a supported nickel, generally after the codimerization catalyst has been eliminated by washing with water. It is sometimes possible to use the codimerization catalyst as a hydrogenation catalyst. After hydrogenation, the unbranched saturated compounds are eliminated by crystallization or by distillation. It is also possible to distill before hydrogenation to concentrate the branched products.

The branched esters can be used as bases for surfactants, emulsifiers, emollients, lubricants or can undergo other treatments, such as transesterification with heavier alcohols when methyl esters are involved initially. It is also possible to transform them into their heavy metal salts.

The following examples illustrate the invention; they are not limiting.

EXAMPLE 1

Preparation of the Catalyst Precursor

Introduced into a Schlenk tube, under an argon atmosphere, are 0.1 mmol of iron$^{(III)}$ tris-acetylacetonate [Fe(acac)$_3$], 0.1 mmol of 2,3-bis(2,6-dimethylphenylimino)butane of formula R—N=CR'—CR'=N—R, with R'=CH$_3$ and R=aryl that is partially substituted by two methyl groups, then 20 ml of conjugated methyl ester of litmus oil, whose composition is as follows: 7.1% of C16:0, 4.0% of C18:0, 29.9% of C18:1, 2.9% of C18:2, unconjugated, and 56.1% of C18:2, conjugated (33.8 mmol). This suspension is heated to 60° C. for 30 minutes, which yields a solution to which 1 mmol of triethylaluminium (TEA), diluted to 10% by volume in n-octane, is added.

Codimerization Catalysis

The entire preceding solution is introduced under an argon atmosphere into a 250 ml autoclave of Hastelloy$^{(R)}$, equipped with a bar magnet stirring mechanism and a double jacket and preheated to 60° C. The reactor is then pressurized to 3 MPa of ethylene and is kept constant during the reaction. At the end of 1 hour, stirring is stopped, and the reactor is depressurized and opened. After the catalyst is eliminated by washing with acidulated water, the mixture that is obtained is analyzed by vapor phase chromatography on a very polar BPX 70-type capillary column with a diameter of 0.32 cm and a length of 50 m. The results appear in Table 1.

The chromatogram of the reaction products is provided, attached (FIG. 2), as well as the chromatogram of the starting product (FIG. 1).

EXAMPLE 2

The solution that is prepared in Example 1, but without the TEA, is introduced into a Hastelloy$^{(R)}$ 250 ml autoclave that is preheated to 60° C. The latter (1 mmol diluted to 10% by volume in n-octane) is introduced into the reactor at 60° C. under an ethylene atmosphere. The reactor is then put at a constant pressure of 3 MPa of ethylene. The reaction is stopped at the end of 1 hour. The results appear in Table 1. According to this table, no difference between these two operating methods is observed.

EXAMPLE 3

The operation is as in Example 1, but the reaction is stopped after 2 hours of stirring. The results appear in Table 1.

EXAMPLE 4 (For Comparison)

The operation is as in Example 1 but without using a ligand. The reaction is stopped at the end of 1 hour. The results appear in Table 1.

EXAMPLE 5 (For Comparison)

The operation is as in Example 1, but the catalytic reaction is carried out at 90° C. The reaction is stopped at the end of 1 hour. The results appear in Table 1.

EXAMPLE 6

The operation is as in Example 5, but at an ethylene pressure of 1 MPa. The reaction is stopped at the end of 1 hour. The results appear in Table 1.

EXAMPLE 7

The operation is as in Example 6, but a reducing agent/metal molar ratio of 7 instead of 10 is used. The reaction is stopped at the end of 1 hour. The results appear in Table 1.

EXAMPLE 8

The operation is as in Example 5, but at an ethylene pressure of 0.1 MPa and by using 4× more (in mmol) of all of the reagents that return to the composition of the catalyst, or 0.4 mmol of iron$^{(III)}$ tris-acetylacetonate [Fe(acac)$_3$], 0.4 mmol of 2,3-bis(2,6-dimethylphenylimino)butane and 4 mmol of triethylaluminum (TEA), diluted at 10% by volume in n-octane. The reaction is stopped at the end of 1 hour. The results appear in Table 1.

EXAMPLE 9 (For Comparison)

The operation is as in Example 5, but the triisobutylaluminium is used as a reducing agent, instead of TEA, at a rate of 1.2 mmol/0.1 mmol of iron. The litmus methyl ester has the same composition as the one that is used and described in Example 1. The reaction is stopped at the end of 1 hour. The results appear in Table 1.

EXAMPLE 10 (For Comparison)

The operation is as in Example 5, but the reducing agent that is used is duisobutylaluminum hydride, at a rate of 2.2 mmol/0.1 mmol of iron. The reaction is stopped at the end of 1 hour. The results appear in Table 1.

EXAMPLE 11 (For Comparison)

The operation is as in Example 5, but at a temperature of 85° C., by using butyl-octyl-magnesium as a reducing agent at a rate of 60 mmol/0.1 mmol of iron. The reaction is stopped at the end of 2 hours. The results appear in Table 1.

EXAMPLE 12 (For Comparison)

The operation is as in Example 1, but iron$^{(III)}$ octoate [Fe(octoate)$_3$] is used instead of Fe(acac)$_3$. The reaction is stopped at the end of 1 hour. The results appear in Table 1.

EXAMPLE 13 (For Comparison)

The operation is as in Example 1, but diphenylphosphinoethane (dppe) instead of 2,3-bis(2,6- dimethylphenylimino)butane is used as a ligand. The reaction is stopped at the end of 1 hour. The results appear in Table 1.

EXAMPLE 14

The operation is as in Example 1, but 2,3-bis(2-methylphenylimino)butane instead of 2,3-bis(2,6-dimethylphenylimino)butane is used as a ligand. The reaction is stopped at the end of 1 hour. The results appear in Table 1.

EXAMPLE 15

The operation is as in Example 1, but bis(2,6-dimethylphenylimino)-ethane instead of 2,3-bis(2,6-dimethylphenylimino)butane is used as a ligand. The reaction is stopped at the end of 1 hour. The results appear in Table 1.

EXAMPLE 16

The operation is as in Example 1, but 2,3-bis(4-methoxyphenylimino)butane instead of 2,3-bis(2,6-dimethylphenylimino)butane is used as a ligand. The reaction is stopped at the end of 1 hour. The results appear in Table 1.

EXAMPLE 17

The operation is as in Example 1, but 2,3-bis(2,6-diisopropylphenylimino)butane instead of 2,3-bis(2,6-dimethylphenylimino)butane is used as a ligand. The reaction is stopped at the end of 1 hour. The results appear in Table 1.

EXAMPLE 18

The operation is as in Example 1, but 2,2-bipyridyl instead of 2,3-bis(2,6-dimethylphenylimino)butane is used as a ligand. The reaction is stopped at the end of 1 hour. The results appear in Table 1.

EXAMPLE 19

The operation is as in Example 1, but an amount that is 10 times larger than all of the reagents involved is used; or 200 ml of conjugated litmus methyl ester, 1 mmol of Fe(acac)$_3$, 1 mmol of ligand 2,3-bis(2,6-dimethylphenylimino)butane and 10 mmol of reducing agent (AlEt$_3$) that is diluted with 10% by volume in n-octane. The reaction is stopped at the end of 3 hours. The results appear in Table 1.

The chromatographic analysis in vapor phase provides a very great selectivity in mono-addition product. Generally no more than 3.5% of di-addition product is observed.

EXAMPLE 20 (For Comparison)

The operation is as in Example 1, but by using a catalytic system that consists of 0.1 mmol of cobalt bis-acetylacetonate and 0.1 mmol of diphenylphosphinoethane and 3 mmol of diethylchloroaluminum. The reaction is stopped at the end of 1 hour. The results appear in Table 1.

EXAMPLE 21

The operation is as in Example 1, but by introducing under ethylene atmosphere 2 mmol of triethylaluminum (TEA) that is diluted with 10% by volume in n-octane, instead of 1 mmol, with the subsequent addition of 0.1 mmol of nickel octoate that is diluted in 5 ml of n-octane. The reaction is stopped at the end of 4 hours. The results appear in Table 1.

EXAMPLE 22

After having undergone a suitable treatment for eliminating all of the aluminum salts as well as the nitrogen-containing ligand, the reaction product that is obtained from Example 19 is totally hydrogenated by using 100 mg of a palladium catalyst on carbon.

The saturated methylester mixture that is obtained after filtration of the palladium on carbon is purified by 2 successive crystallization operations in acetone at −20° C. After elimination of the majority of palmitate and methyl stearate, the addition compound, after the acetone has evaporated, remains liquid up to a temperature of −30° C.

The vapor phase chromatography indicates that the compound contains 3.3% of methyl palmitate, 1.0% of methyl stearate, 91.5% of mono-addition products, 3.2% of di-addition products and 1% of methyl behenate.

The chromatogram of the purified product is provided, attached (FIG. 3).

The NMR of the hydrogen provides a proton signal at 1.8 ppm corresponding to 1 proton on a tertiary carbon. It is primarily the NMR of the product before hydrogenation that provides several indications on the vinyl group between 4.9 and 5 ppm that was absent in the initial product and that corresponds to a double terminal bond or a methyl vinyloctadecenoate-type compound.

Table 1 groups the results of Examples 1 to 21, which relate to the addition of ethylene to a methyl ester of conjugated litmus oil. In this Table 1, the conversion of conjugated linoleates and the conversion of addition product relative to the initial conjugated ester have been considered. The catalyst is an iron salt that is generally reduced by AlEt$_3$ that is diluted in n-octane, except where another solvent or another reducing agent is indicated.

TABLE 1

| Addition of Ethylene to a Methyl Ester of Conjugated Litmus Oil | | |
|---|---|---|
| Example | Conversion of Conjugated C18:2 (% by weight) | Conversion of Mono-Addition Products (% by weight) |
| 1 | 82 | 80 |
| 2 | 82 | 80 |
| 3 | 100 | 97 |
| 4 | 0 | 0 |
| 5 | 60 | 59 |
| 6 | 49 | 49 |
| 7 | 27 | 27 |
| 8 | 72 | 71 |
| 9 | 40 | 40 |
| 10 | 22 | 22 |
| 11 | 10 | 10 |
| 12 | 80 | 79 |
| 13 | 22 | 22 |
| 14 | 26 | 26 |
| 15 | 5 | 5 |
| 16 | 21 | 21 |
| 17 | 8 | 8 |
| 18 | 12 | 12 |
| 19 | 98 | 95 |
| 20 | 4 | 4 |
| 21 | 100 | 68* |

*The addition (32%) being the di-addition products.

Comments on the Results that are Obtained Effect of the Temperature

The results of Examples 1 to 3 that operated at a temperature of 60° C. provide higher conversions than the one that is obtained in Example 5, which worked at a temperature of 90° C.

Influence of the Pressure

Example 6 that operates at a pressure of 1 MPa is less capable than Examples 1 to 3 that worked at 3 MPa of ethylene pressure.

Influence of the Ligand

Example 4 (for comparison) shows that a catalytic system without a ligand is totally inactive.

Example 13 that uses a phosphorus-containing ligand of the diphenyl-phosphino-ethane type is clearly less capable than the 2,3-bis(2,6-dimethylphenylimino)butane that is used in Example 1.

The catalytic systems of Examples 14 to 18 that use nitrogen-containing ligands are less capable than Examples 1 to 3 that use the 2,3-bis(2,6-dimethylphenylimino)butane.

Influence of the Reducing Agent

An aluminum to metal stoichiometry that is close to 10 (Examples 1 to 3) provides better results than a lower stoichiometry, close to 7 (Example 7).

Examples 9, 10 and 11 (for comparison with Example 1), which used reducing agents other than triethylaluminum, remain less capable.

Nature of the Iron Salt

Test 12 that used iron(III) octoate in place of the iron(III) acetylacetonate provides identical results.

Catalytic Activity

Comparison of the activity of the catalytic system, with an iron base of the invention (Example 1), with that of cobalt (Example 20) shows an activity that is 20 times greater for the system with an iron base at the same metal concentration.

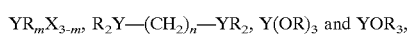

What is claimed is:

1. Process for obtaining a codimer, characterized in that at least one monoolefinic compound is added to a fatty substance that comprises at least two conjugated or unconjugated ethylene bonds, in the presence of a catalytic system that comprises at least one iron compound, at least one reducing compound, and at least one ligand that contains phosphorus, arsenic, antimony or nitrogen.

2. Process according to claim 1, wherein in said catalytic system:

said iron compound corresponds to formula Fe $X_n$, in which n=2 or 3, and X represents a halide, a thiocyanide, a sulfate, a nitrate, an alcoholate, a carbonate, a carboxylate, a diketone, a betacetocarboxylic acid ester, a hydroxyl, an alkyl or alkenyl group or a hydride;

said reducing agent corresponds to one of formulas $AlR_X(X)_{3-X}$, $LiAlH_4$, $NaBH_4$ or $LiAlH_n(OR)_{4-n}$, in which R=alkyl, X=halide and n=1, 2 or 3, or consists of an aluminoxane or an organo-magnesium compound;

and said ligand is selected from among the derivatives of phosphorus, arsenic or antimony that correspond in general to the formulas:

$YR_mX_{3-m}$, $R_2Y—(CH_2)_n—YR_2$, $Y(OR)_3$ and $YOR_3$, in which Y=P, As or Sb; m=0, 1, 2, or 3; R=alkyl, aryl or substituted aryl; X=halogen, and n=0, 1, 2, 3 or 4;

and from among the nitrogen-containing ligands, amines and polyamines, imidazole, substituted imidazoles, pyrrole and substituted pyrroles, pyrazoles, amidic derivatives, imines, diimines, and pyridinic derivatives.

3. Process according to claim 1, wherein said monoolefinic compound is selected from among the monoolefinic hydrocarbons such as ethylene, propylene, or butene-1.

4. Process according to claim 1, wherein said fatty substance that comprises at least two ethylene bonds is selected from among the diene or polyene fatty substances that are conjugated or can be conjugated, whereby the number of carbon atoms of the fatty chain comprises 18 to 26 carbon atoms on the chain that carries the carboxylic group, with the latter being linked to a mono-, di-, tri- or tetrafunctional alcohol with 1 to 18 carbon atoms.

5. Process according to claim 1, wherein the catalytic system comprises, as an iron compound, halides, acetylacetonates, or carboxylates and, as a reducing agent, a system with an alkylaluminum base, which may or may not be substituted, or aluminoxane or aluminum or boron hydrides, and wherein the molar ratio between the reducing agent and the iron is 1 to 30.

6. Process according to claim 1, wherein the ligand that is introduced is a diimine that has as its formula R—N=CR'—CR'=N—R, with R'=H or CH3 and R=alkyl, aryl or aryle that is partially substituted by 1, 2 or,3 methyl, ethyl, isopropyl or methoxy groups.

7. Process according to claim 1, wherein the molar ratio between the ligand and the iron is 0.5 to 10.

8. Process according to claim 1, wherein the iron concentration is $10^{-4}$ to $10^{-1}$ mol of iron per mol of conjugated polyunsaturated fatty substance, the reaction temperature is 40 to 120° C., and the olefin pressure is 0.1 to 30 MPa.

9. Process according to claim 1, wherein the ester that is employed is conjugated in advance with an alkaline alcoholate-type system or conjugated during the addition with the same system as the one that makes possible the addition of olefin.

10. Process according to claim 9, wherein the ester that is employed is conjugated during the addition of olefin or before with an iron catalyst that is co-catalyzed by traces of at least one transition metal that is selected from among nickel, copper, rhodium and palladium.

11. Process according to claim 1, wherein the catalyst is a mixed system that is obtained by reaction, on the one hand, of an $FeHXL_2$ or FeHXL' complex, where X is an anion, halogen, or carboxylate, L is an imine and L' is a diimine, introduced in a 1:2 molar ratio relative to the iron for the iron complex that contains L, and in a 1:1 molar ratio relative to the iron for the iron complex that contains L' and, on the other hand, a reducing agent.

12. Process according to claim 1, wherein the olefinic compound that is produced by codimerization contains one or more links whose length corresponds to the olefin that is employed.

13. Branched compounds, wherein they are obtained by a process according to claim 1.

14. Process for preparation of saturated branched compounds by hydrogenation of branched compounds according to claim 13, wherein the unsaturated branched compounds are hydrogenated in the presence of the codimerization catalyst or a known hydrogenation catalyst, optionally after filtration or elimination of the codimerization catalyst.

15. Process according to claim 14, wherein the saturated branched compound that is obtained by hydrogenation is then purified after the branched compounds are separated by distillation and/or by elimination of the unbranched saturated compounds by crystallization in a solvent.

16. Saturated branched compound that is obtained by a process according to claim 15.

17. A process comprising employing a saturated branched compound according to claim 16 as a base for surfactants, emulsifiers, emollients, lubricants or heavy metal salts.